United States Patent [19]

Siposs

[11] 4,344,777
[45] Aug. 17, 1982

[54] DIRECTED FLOW BUBBLE TRAP FOR ARTERIAL BLOOD

[76] Inventor: George G. Siposs, 2855 Velasco La., Costa Mesa, Calif. 92626

[21] Appl. No.: 109,801

[22] Filed: Jan. 7, 1980

[51] Int. Cl.³ .............................................. B01D 19/00
[52] U.S. Cl. ....................................... 55/178; 55/201; 210/436; 210/456
[58] Field of Search ............... 210/DIG. 23, 440, 443, 210/444, 436, 472, 499, 456, 418, 421, 137, 94; 55/178, 201, 52

[56] References Cited

U.S. PATENT DOCUMENTS

| | | | |
|---|---|---|---|
| 2,018,901 | 10/1935 | Rush | 210/436 X |
| 2,469,917 | 5/1949 | Curtis | 55/52 X |
| 3,242,643 | 5/1966 | Moore et al. | 55/52 X |
| 3,468,614 | 9/1969 | Nilsson | 55/52 X |
| 3,681,562 | 8/1972 | Winzen | 210/94 |
| 3,701,433 | 10/1972 | Krakauer et al. | 210/DIG. 23 |
| 3,720,316 | 3/1973 | Riesbeck et al. | 210/456 |
| 3,765,536 | 10/1973 | Rosenberg | 210/DIG. 23 |
| 3,782,082 | 1/1974 | Rosenberg | 210/DIG. 23 |
| 3,859,216 | 1/1975 | Sisson et al. | 210/440 |
| 3,891,416 | 6/1975 | Leonard et al. | 210/DIG. 23 |
| 4,056,476 | 11/1977 | Mouwen et al. | 210/DIG. 23 |
| 4,075,099 | 2/1978 | Pelton et al. | 210/443 |
| 4,140,500 | 2/1979 | Koponen | 55/201 |
| 4,164,468 | 8/1979 | Raible | 210/DIG. 23 |

Primary Examiner—Frank A. Spear, Jr.
Attorney, Agent, or Firm—Allen A. Dicke, Jr.

[57] ABSTRACT

The arterial blood filter of this invention is for extra-corporeal bypass during cardio-pulmonary surgery. It has an internal divergent blood flow path from the inlet to smoothly reduce blood flow velocity to permit separation of air bubbles with minimum trauma to blood cells. The upper portion of the blood filter housing permits collection of air bubbles and permits their withdrawal. The inlet and outlet connections to the filter are both on the bottom to ease draping of the connecting tubes.

24 Claims, 9 Drawing Figures

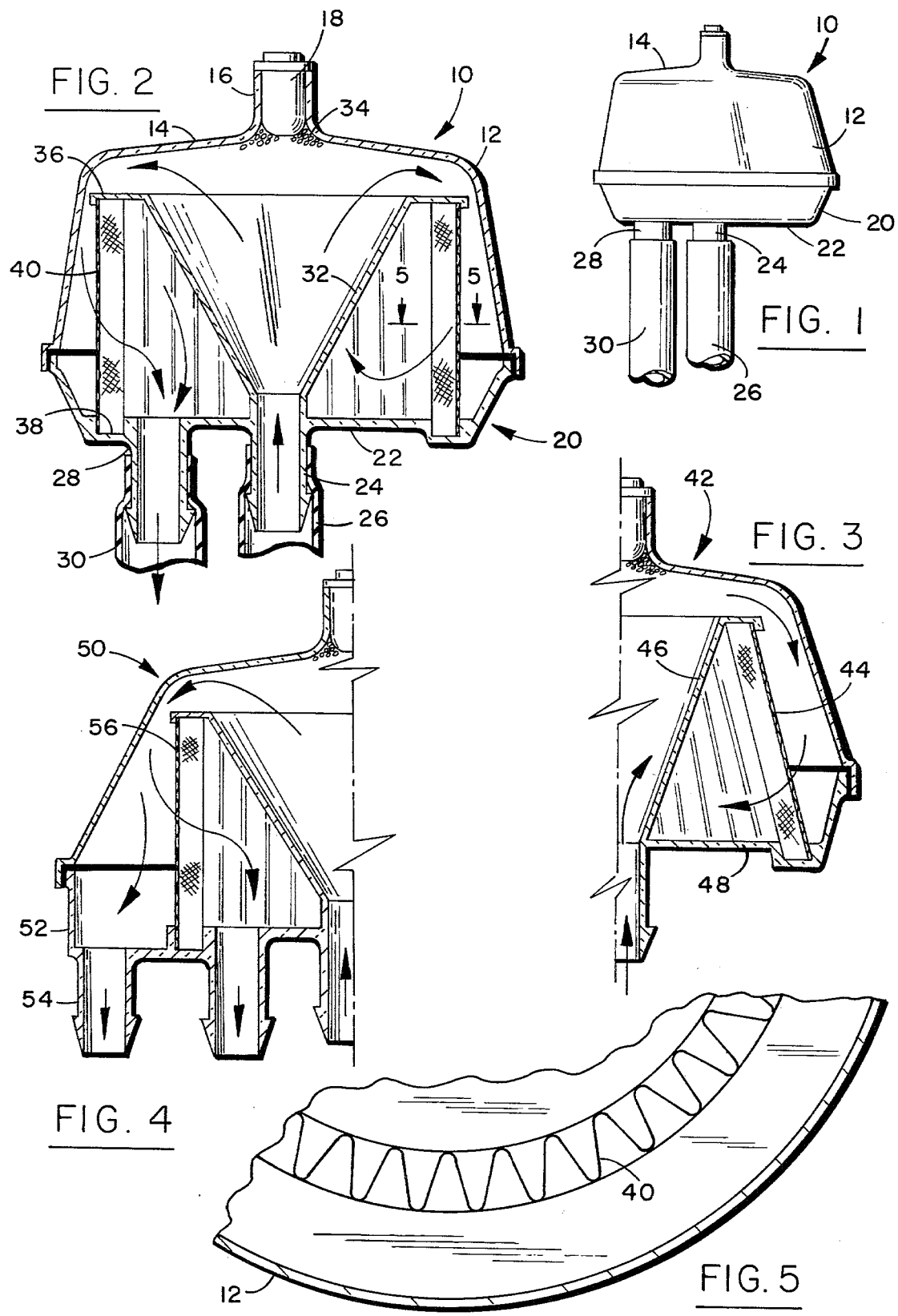

DIRECTED FLOW BUBBLE TRAP FOR ARTERIAL BLOOD

BACKGROUND

This invention is directed to an arterial blood filter specifically designed for use in extra-corporeal blood bypass circuits as are often used in cardio-pulmonary surgery.

One type of blood filter in the prior art is the type that may be used for slow flow and single pass filtration such as for the filtering of blood from blood bank bags or intravenous solutions. These filters have large pores and mainly filter out clots and large debris. However, in the filtration of blood in an extra-corporeal blood circuit employed during open-heart surgery, there are relatively high flow rates going up to 6.5 liters per minute (and repeated recirculation of the blood through the circuit).

At present, there are two kinds of filters used for extra-corporeal blood circuit filtration in the cardio-pulmonary bypass situations. One is sold by Swank and is the form of a filter which has matted fibers in a 3-dimensional structure to provide a depth filter. The fibers may have a sticky surface so that the blood elements may adhere to it. In some cases, this kind of filter plugs up fast and restricts or stops blood flow. Furthermore, when the filter is of a depth construction, it is more likely to filter out even the desirable blood elements such as white cells.

Another available filter is basically a single layer woven filter screen of approximately 20 to 50 micron pore size. This filter has a single surface interposed in the blood flow stream. A surface area of approximately 100 square inches is employed for the intended flow. Sometimes, the filter material is metallic wire, and sometimes it is polymer composition material. In the case of polymer composition material, it may or may not be thermoplastically bonded at the crossover points. Furthermore, the prior patents speak of both simple weaving and twill weaving of the strands. Such filters are available from the Pall Corporation of Glen Cove, N.Y., as exemplified by Rosenberg U.S. Pat. No. 3,696,932 and Krakauer et al. U.S. Pat. No. 3,701,433. Such filters are also available from Johnson and Johnson, New Brunswick, N.J. as exemplified by Mouwen et al. U.S. Pat. No. 4,056,476. These companies appear to be the present principal suppliers of disposable blood filters used for extra-corporeal blood bypass circuits.

However, such blood filters have functional problems so that there is room for substantial improvement as becomes clear from the description of the blood filter of this invention.

SUMMARY

In order to aid in the understanding of this invention, it can be stated in essentially summary form that it is directed to a blood filter which incorporates a divergent blood flow passage at the inlet thereof to decrease blood velocity in a manner as to minimize trauma to the blood cells, and at the same time provide a filter design which aids in the phase separation of gas bubbles in the blood flow stream, by providing a low velocity zone in which the gas bubbles can separate.

It is thus an object of this invention to provide a blood filter which is particularly useful for the filtration of blood in an extra-corporeal blood flow circuit during cardiopulmonary bypass so that properly filtered blood, with minimum trauma to the cells therein, is continuously circulated. It is another object to separate air bubbles by hydraulic means, even before they are stopped by the "bubble point" of the screen filter. It is a further object to provide a filter design which reduces blood turbulence to reduce hemolysis. It is another object to provide a convenient place where air bubbles can congregate and can be exhausted from the system. It is another object to provide a blood filter having a design with both inlet and outlet tubes in the bottom to eliminate buckled lines and provide convenient connections. It is a further object to provide a blood filter for extra-corporeal blood filtration which reduces the volume of blood required to prime the lines and the blood filter.

Other objects and advantages of this invention will become apparent from a study of the following portion of the specification, the claims and the attached drawings.

BRIEF DESCRIPTION OF THE DRAWINGS

FIG. 1 is a side-elevational view of a first preferred embodiment of the blood filter of this invention.

FIG. 2 is an enlarged transverse section therethrough on its center line.

FIG. 3 is a central section through a second preferred embodiment of the blood filter of this invention, with parts broken away.

FIG. 4 is a central section through a third preferred embodiment of the blood filter of this invention, with parts broken away.

FIG. 5 is an enlarged section taken through the filter element as seen generally along the line 5—5 of FIG. 2, with parts broken away.

DESCRIPTION OF THE PREFERRED EMBODIMENTS

Figure 7:
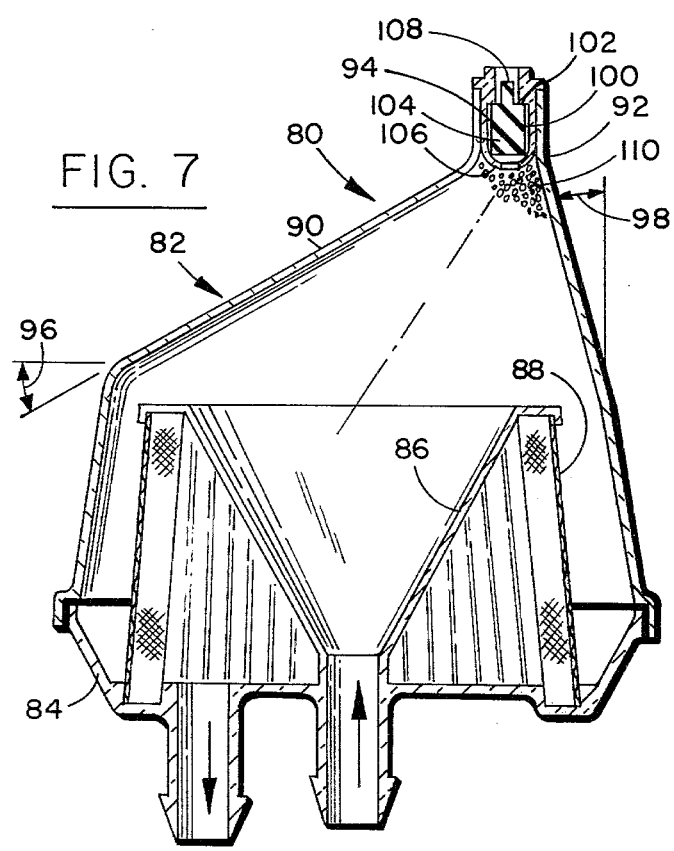
FIG. 7 is a center line section through a fifth preferred embodiment of the blood filter of this invention.

FIGS. 1 and 2 illustrate the first preferred embodiment of the blood filter of this invention where it is generally indicated at 10. Blood filter 10 has a bell-shaped upper housing 12 which has a somewhat upwardly directed conical top 14 which terminates in valve boss 16 in which is located valve 18. Valve 18 has a resiliently compressed inner stop member which can be downwardly urged off its seat by insertion of a small rod from the top. Valve 18 is an air valve which can thus be manually actuated to release air from the upper interior of the bell housing. Upper housing 12 is preferably of transparent synthetic polymer composition material so that it can be readily formed and the presence of air bubbles can be visually detected so that they can be released by opening air valve 18.

Lower housing 20 has a bottom 22 in which is positioned inlet fitting 24. As seen in FIG. 2, the inlet fitting has a barb thereon to easily and securely receive inlet tube 26. Adjacent to inlet fitting 24, also formed on bottom 22, is outlet fitting 28 to which is secured outlet tube 30. Outlet fitting 28 is also a barbed fitting for the secure attachment of the outlet tubing. The fittings are of appropriate diameter to receive tubing of suitable size for the particular cardiopulmonary bypass arrangement. Both of the fittings are downwardly directed so that the attached tubing drapes naturally when it is full of blood. No special tubing support is required to prevent tube kinking as compared to systems which have a tube fitting extending out of the top.

Within lower housing 20 is positioned flow cone 32. Flow cone 32 is attached near its apex to the bottom 22 to receive the blood flow upwardly in inlet tubing. The spread of the cone in the upward direction permits smooth reduction in blood velocity. At clinical flow rates, blood velocity in the ⅜ inch inlet line 26 is approximately 37 inches per second. The upper end of flow cone 32 has an area approximately 25 times the inlet area so that the average blood velocity at the open, upper end of flow cone 32 is about 1.5 inch per second. This lower velocity reduces the trauma of blood cells which would otherwise impinge upon the flat inner surface of top 14 at high velocity. Furthermore, it permits the gravitational separation of air bubbles in the blood. If there are any air bubbles in the blood, they have enough time to rise up and inside of the conical top 14 and collect in the air zone 34 where they can be released out through air valve 18. After the decrease in velocity, the blood flow turns radially outward and then downward around the outer interior of upper housing 12.

Flow cone 32 carries flange 36 arounds its upper exterior. Recess 38 is formed in lower housing 20 and facing flange 36. Filter member 40 is engaged therebetween. The medium of filter member 40 is a corrugated filter screen with its ends engaged against flange 36 and in recess 38. The medium of the filter screen is a corrugated synthetic polymer composition mesh or a stainless steel wire mesh. The polymer composition mesh may be a polyester monofilament woven screen having openings in the range of 20 to 60 microns and having a filament diameter in the 20 to 60 micron range. The filter fabric is preferably a thermoplastic polymer composition material, including nylon, which may be thermoplastically joined at the woven contact points of the fabric. The fabric may be either square or a twill-weave, providing the open areas are uniformly arranged. Alternatively, a molded microporous complex having omnidirectional interconnecting openings of 20 to 60 microns, made from a polymer plastic (such as polyethylene which is hydrophobic) may be used. Such are available from Glasrock Products, Fairburn, Ga.

The filter fabric medium is formed into the corrugated (multipointed) configuration and circular structure and is potted into recess 38 at the bottom and potted against the underside of flange 36. The potting gives rigidity to the ends of the structure, and the corrugations provide the rigidity over the surface area which is also enlarged by employment of the corrugations. Potting is accomplished by securing the two ends of the filter fabric in their position at the time the cone 32 is adhesively attached in place at its apex at the inlet. Thus, the filter is secured in place while it may still be inspected, and thereafter, the upper housing is adhesively secured to the lower housing around the circumferential interengaging flanges thereon. An appropriate adhesive is used. The upper and lower housings 12 and 20 as well as the flow cone 32 are preferably made of polycarbonate synthetic polymer composition material which provides the desirable transparency, is tough to inhibit breakage, and can be ultrasonically welded or solvent-bonded.

Most of the mesh screens employed in blood filtration, that is, from 20 to 60 micron openings, provide a good barrier to the passage of air. This is because, when they are coated with blood, the blood has a certain amount of surface tension in the blood filter opening so that some pressure is required to cause the air to be driven through. This is called the bubble point. In the present filter described in this disclosure, the resistance to air passage is greatly enhanced by the flow pattern which causes much lower blood velocity in the approach to the filter member so that the buoyancy of the air in the blood has a substantial amount of time to permit the bubbles to be separated and caught in the upper housing instead of being washed down against the filter screen.

The corrugated structure of the filter fabric together with its securement at both ends provides a stable structural member which prevents its collapse. Collapse would close up some of the pores and would liberate caked blood emboli which then might be able to float to the patient and cause harm or occlude flow in the line. Since there is little axial stress in the filter fabric, after the fabric is potted at both ends, the corrugated filter fabric member will not collapse from such causes. A second, much coarser layer of mesh 129 may be used on the inner surface of the primary filter mesh to keep the adjacent corrugations apart and to ensure a good flow path. A third, coarse layer 130 may be on the outside also to keep corrugations apart.

As the blood enters and proceeds upward through cone 32, the natural buoyancy of the air bubbles and the slow velocity of the blood make it easy for the bubbles to collect under the valve 18 where the bubbles can be exhausted by slow, continuous purging or periodic siphoning by syringe, or periodic venting. The upper housing of the filter is a very efficient bubble collection chamber which reduces the chance of air embolization in the arterial line. Localizing the air bubbles is accomplished atraumatically as a "first line of defense" before the bubbles reach the screen cloth. This is accomplished without additional filter bulk. The "second line of defense" against air in the line is the bubble point of the filter fabric.

FIG. 3 illustrates a blood filter 42 which is configured with a conical filter member 44. The flow cone 46 and lower housing 48 are configured with their filter medium receiving grooves such that the filter medium 44 is configured into a corrugated conical structure. When the conical shape of the filter member 44 has the same angle as the bell shape of the upper housing, then smooth flow is enhanced downwardly around the outer inside of the upper housing and downward along the outside of the conical filter member 44. The other structure is the same as in blood filter 10 because the conical shape of the filter 42 changes the proportions of the parts, as indicated. The conical structure of the filter member 44 aids in producing strength therein.

Blood filter 51 illustrated in FIG. 4 is another preferred embodiment of the blood filter of this invention. It is the same as the blood filter 10, but the lower housing 52 also carries an outlet 54 thereon exterior to the filter member 56. Thus, outflow through outlet 54 is unfiltered and is used in those cases where the filter member is plugged up but system flow must continue.

Bypass outlet 54 is connected by flexible tube to the regular outlet tube. A clamp normally closes the bypass outlet, which can be opened if required.

Figure 6:
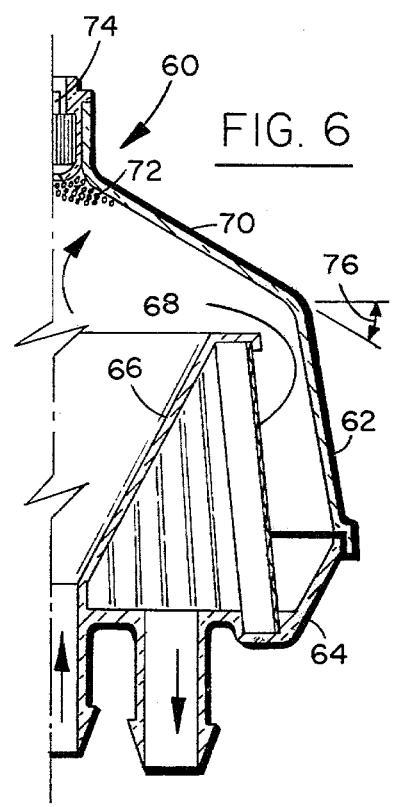
FIG. 6 is a sectional view taken along the center line, similar to FIG. 2, showing a fourth preferred embodiment of the blood filter of this invention, with parts broken away.

The trauma previously inflicted on the blood is thus reduced by reducing the average velocity of the blood before it turns. Flow cone 32 reduces the average blood velocity. The separation of air bubbles from the flowing blood is a function of the blood velocity, the angle under the top 14, and the space thereunder. In FIG. 6, the blood filter 60 is shown as having an upper housing 62 and a lower housing 64 with an internal flow cone 66 secured into the lower housing and securing blood filter member 68, which in this case is slightly conical to conserve volume. As has been previously described, the medium of blood filter member 68 is a corrugated, woven fabric which is potted at the top into a circular recess in the underside of the upper part of flow cone 66 and its lower edge into a circular recess in lower housing 64. By increasing the angle of top 70 of upper housing 62, there is more gravitational force to permit the bubbles 72 to rise up to valve 74, especially with higher blood flow rates. In the embodiment shown, the angle 76 is about 30 degrees. In FIG. 6, the structure is broken away at the center line, with the valve 74 on the center line and with most of the structure formed as a body of revolution about that center line.

The blood filter 80 is another preferred embodiment of the blood filter of this invention. Blood filter 80 has an upper housing 82 which has an asymmetrical cone and lower housing 84. The lower housing, including flow cone 86 and filter member 88, is identical to the same structure as FIG. 6 and is virtually the same as the structure illustrated and described with respect to FIGS. 1, 2 and 3. There is no difference between the lower housing 84 and the lower housing 20.

Upper housing 82, however, is different in that its top 90 is no longer in the form of a right circular cone as its top 70, but is an offset cone. Neck 92 is substantially cylindrical and upright and contains valve 94 of the same structure as valve 18. Neck 92 is offset from the center line as shown, and the top 90 is formed so that the lowest angle 96 is about 30 degrees and its highest angle 98 is about 15 degrees from the upright axis.

Figure 8:
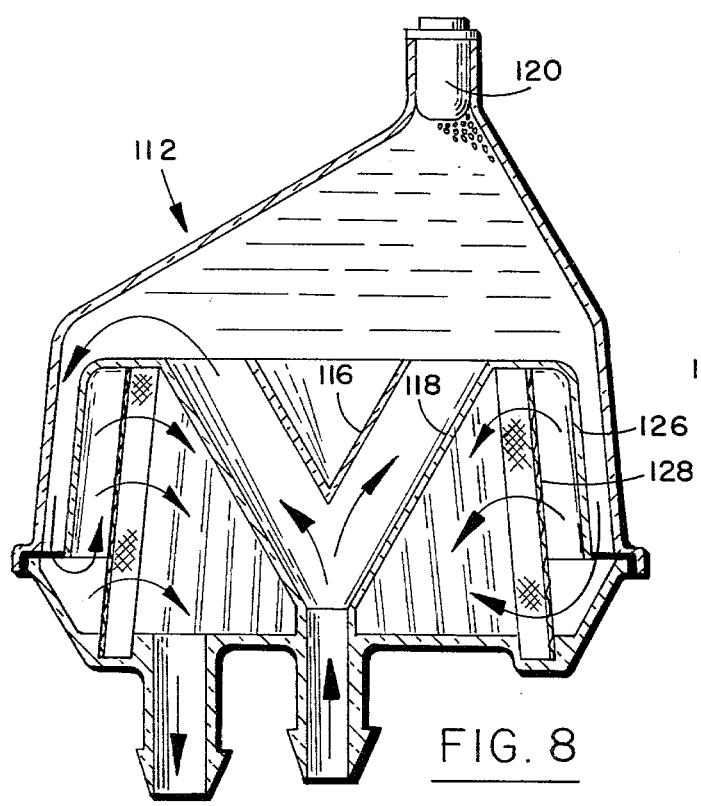
FIG. 8 is a section similar to FIG. 7, with parts broken away, showing another arrangement of internal flow-directing devices.
Figure 9:
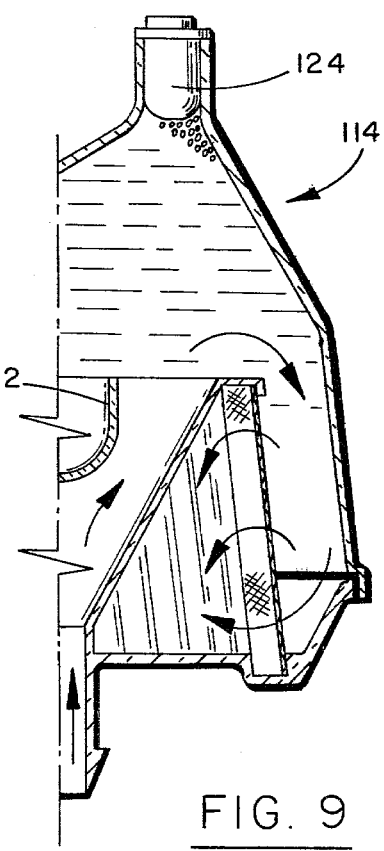
FIG. 9 is a sectional view showing a further arrangement of a slow directing device.

The offset structure of the neck 92 in upper housing 82, also shown in FIGS. 8 and 9, has the advantage of developing an unsymmetrical flow pattern. At high flow rates, the flow through the volume under an upper housing which is a structure of revolution about a center line, such as illustrated in FIGS. 1 through 4 and 6, has a tendency to keep the small air bubbles entrained in blood flow and washed away from the valve 102. By changing the flow pattern to produce a more quiet area, as in the structures of FIGS. 7, 8 and 9, the bubbles rise more naturally and easily into the more quiet zone under the top 90 at the bottom of neck 92. Air bubble separation may be enhanced by moving neck 92 farther upward and farther to the side, but raising the position of the neck 92 increases the priming volume. The angles indicated in FIG. 7, with angle 96 being between 30 and 45 degrees, appear to be most satisfactory in view of the different system requirements.

Valve 94 has a body 100 which has a shoulder 102. The body 100 may be of injection-molded thermoplastic material of suitable stability and non-toxic characteristics. Valve member 104 is made of resilient material and is positioned against shoulder 102. Body 100 is thermoplastically crimped over valve member 104 to form retainer 106 to hold valve member 104 in place. Furthermore, valve member 104 is compressed when the retainer is formed so that valve member 104 resiliently engages against shoulder 102. Neck 108 extends partway up through the outlet opening in the top of body 100 and can be engaged and depressed by a syringe tip or the like to thrust the valve member off of shoulder 102 to open the valve. Valve member 104 is scored around its outer body to prevent sealing around its outer periphery or along its lower corners so that pressing valve member 104 down away from shoulder 102 causes valve opening. Valve opening permits release of the bubbles 110 which congregate underneath the valve. This valve is commercially available from Halkey-Roberts Corp., Paramus, N.J. It is the type used for air-sealing the cuff balloon of an endotracheal tube. A conventional Luer-lock opening with cap may be employed instead. Upper housing 82 is preferably formed of transparent material so that the accumulation of bubbles may be observed and consequently released.

Blood filter 112 in FIG. 8 and blood filter 114 in FIG. 9 are further preferred embodiments of the blood filter of this invention. The upper and lower housings of the blood filters 112 and 114 are the same as described for the blood filter 80 of FIG. 7. In order to provide a more quiet zone in the upper part of blood filter 112 under its upper housing adjacent its air valve, distributor cone 116 is positioned inside of its flow cone 118. Distributor cone 116 creates an eddy pattern which causes the air bubbles in the inflowing blood to separate and gather directly up above cone 116 and under air valve 120. Distributor cone 116 causes eddys in the flow which enhance the separation. Distributor cone 116 does not present a trauma-inducing flat surface toward the incoming blood flow, and flow cone 118 still provides the function of uniformly and without trauma reducing the flow velocity. Blood filter 114 has a similar structure in distributor 122. Distributor 122 presents a hemisphere toward the blood flow and a short cylinder above the hemisphere which extends to a level at the top of the inlet flow cone. Distributor 122 also provides the turbulence under the upper part of the upper housing to permit the air bubbles to gather under valve 124 whence they may be released.

Blood filter 122 also has shield 126 which is formed as part of the flow cone and extends downwardly from half to two-thirds the length of the filter member 128. Shield 126 lengthens the path that air bubbles have to take before they reach the filter member 128 and thus provides more time for the air bubbles to separate. Of course, the filter member 128 itself will stop the air bubbles, but it is better practice to capture the air bubbles in a place where they can be released before the filtration phase.

This invention has been described in its presently contemplated best mode, and it is clear that it is susceptible to numerous modifications and modes and embodiments within the ability of those skilled in the art and without the exercise of the inventive faculty. Accordingly, the scope of this invention is defined by the scope of the following claims.

What is claimed is:

1. A directed flow bubble trap and arterial blood filter comprising:
   a housing;
   inlet means for permitting and controlling the upward inlet flow of arterial blood into said housing to substantially fill said housing, said inlet means including an upwardly directed divergent flow control member for causing a reduction in flow velocity as the arterial blood flows upward in said upwardly divergent flow control member and for causing flow with a radially outward component at the top of said upwardly divergent flow control member, said upwardly divergent flow control member being open to permit generally unobstructed radial outward flow at its larger end for reducing blood velocity so that blood velocity at the top of said upwardly divergent flow control member in said housing is lower than in said inlet, a low flow velocity volume in the top of said housing above said upwardly divergent from control member so that air bubbles released from the arterial blood can separate upwardly into said low flow velocity volume, said housing top having an outlet valve therein for the release of air collected within the top of said housing;

a blood filter member in said housing, said blood filter member having first and second sides and positioned around said upwardly divergent flow control member so that arterial blood leaving said upwardly divergent flow control member flows downward and reaches said first side of aid filter member;

an arterial blood outlet on said housing, said arterial blood outlet being connected to said housing so that it is positioned on the second side of said filter member to receive therefrom air separated and filtered arterial blood.

2. The blood filter of claim 1 wherein said filter housing has a top and a bottom and both said inlet and said outlet are positioned on said housing bottom.

3. The blood filter of claim 2 wherein there is a second outlet on the bottom of said housing, said second outlet being positioned laterally outside of the inlet surface of said filter member so that unfiltered blood may pass out of said housing out through said second outlet by bypassing the filter.

4. The blood filter of claim 1 wherein said top is in the form of a right circular cone.

5. The blood filter of claim 4 wherein said filter housing has a bottom and both said inlet and said outlet are positioned on the bottom of said housing.

6. The blood filter of claim 1 wherein said top is substantially a slanted cone.

7. The blood filter of claim 6 wherein said filter housing has a bottom and both said inlet and said outlet are positioned on the bottom of said housing.

8. A directed flow bubble trap and arterial blood filter comprising:

a housing;

inlet means for permitting and controlling the upward inlet flow of arterial blood into said housing to substantially fill said housing, said inlet means including an upwardly divergent, substantially conical flow control cone for causing flow with a radially outward component at the top of said upwardly divergent flow control cone, said upwardly divergent flow control cone being open to permit generally unobstructed radially outward flow at its larger end for reducing blood velocity so that the blood velocity at the top of said upwardly divergent flow control cone in said housing is lower than in said inlet, said housing top having an outlet therein for the release of air collected within the top of said housing;

an arterial blood filter member in said housing, said arterial blood filter member having first and second sides and positioned around said upwardly divergent flow control cone so that arterial blood leaving said upwardly divergent flow control cone flows down around said blood filter member and reaches said first side of said arterial blood filter member; and an arterial blood outlet on said housing, said arterial blood outlet being connected to said housing so that it is positioned on the second side of said arterial blood filter member.

9. The blood filter of claim 8 wherein said filter member is secured on said flow cone and on said housing and is positioned to surround said flow cone so that said flow cone serves as structural support for the upper edge of said filter member.

10. The blood filter of claim 9 wherein said filter member is made of a filter medium which is a porous structure having omnidirectional interconnecting pores made of polyethylene or polypropylene or fluorocarbon material.

11. The blood filter of claim 8 wherein a flow director is positioned within said inlet cone to distribute blood flow rising in said inlet flow control cone to produce a zone above flow control member wherein air bubble separation is enhanced.

12. A directed flow bubble trap and arterial blood filter comprising:

a housing;

inlet means for permitting and controlling the upward inlet flow of arterial blood into said housing to substantially fill said housing, said inlet means including an upwardly divergent, substantially conical flow control cone for causing flow with a radially outward component at the top of said upwardly divergent flow control cone, said upwardly divergent flow control cone being open to permit generally unobstructed radially outward flow at its larger end for reducing blood velocity so that the blood velocity at the top of said upwardly divergent flow control cone in said housing is lower than in said inlet, said housing top having an outlet therein for the release of air collected within the top of said housing;

an arterial blood filter member in said housing, said arterial blood filter member being a corrugated filter medium of woven monofilament screen having between 20 to 60 microns pore size and having first and second sides, said blood filter member being positioned around to surround said flow cone and being secured to said flow cone and to said housing so that said flow cone serves as a support for the upper edge of said filter member so that arterial blood leaving said upwardly divergent flow control cone flows down around said blood filter member and reaches said first side of said arterial blood filter member; and an arterial blood outlet on said housing, said arterial blood outlet being connected to said housing so that it is positioned on the second side of said arterial blood filter member.

13. The blood filter of claim 12 wherein said filter housing has a top and a bottom and both said inlet and said outlet are positioned on the bottom of said housing.

14. The blood filter of claim 13 wherein said inlet fitting is substantially on the bottom center of said housing and said outlet fitting extends out of the bottom of said housing beside said inlet fitting.

15. The blood filter of claim 12 wherein said woven screen is made of woven thermoplastic synthetic polymer composition material.

16. The blood filter of claim 12 wherein said filter screen is made of woven stainless steel wire.

17. The blood filter of claim 12 wherein said screen is woven of substantially 35 micron monofilament to provide substantially 37 micron pores to present a substantially 15 percent open area.

18. The blood filter of claim 17 wherein the woven screen is a plain woven screen.

19. The blood filter of claim 17 wherein the woven screen is a twill woven screen.

20. The blood filter of claim 12 wherein said screen is woven of substantially 30 micron monofilament to provide substantially 41 micron pores to present a substantially 33 percent open area.

21. A directed flow bubble trap and arterial blood filter comprising:
a housing;
inlet means for permitting and controlling the upward inlet flow of arterial blood into said housing to substantially fill said housing, said inlet means including an upwardly directed divergent flow control cone causing reduction in flow velocity as the arterial blood flows upwardly in said upwardly directed divergent flow control cone and for causing flow with a radially outward component at the top of said upwardly divergent flow control cone for reducing blood velocity so that blood velocity at the top of said upwardly divergent flow control cone in said housing is lower than in said inlet, a flow control director within said inlet flow control cone, said director being a cone with its apex directed downwardly toward said inlet in said inlet flow control cone;
an arterial blood filter member in said housing, said arterial blood filter member having first and second sides and being positioned around said upwardly divergent flow control cone so that arterial blood leaving said upwardly divergent flow control cone flows down and reaches said first side of said filter member; and
an arterial blood outlet on said housing, said arterial blood outlet being connected to said housing so that it is positioned on the second side of said filter member, said housing having a top outlet thereon for release of air collected within the top of said housing.

22. A directed flow bubble trap and arterial blood filter comprising:
a housing;
an upwardly directed divergent flow control cone positioned within said housing;
inlet means connected to said housing and to said flow control cone for directing the upward inlet flow of arterial blood into said housing to fill said housing, said upwardly directed divergent flow control cone causing reduction in flow velocity as the arterial blood flows upwardly in said upwardly directed divergent flow control cone and causing flow with a radially outward component at the top of said upwardly divergent flow control cone for reducing blood velocity so that blood velocity at the top of said upwardly divergent flow control cone in said housing is lower than in said inlet to permit air to separate and rise to the upper interior of said housing, a flow control director within said inlet flow control cone, said director being at least partly spherical and having its spherical portion directed downwardly toward said inlet of said flow control cone; and
air outlet means connected to said housing for releasing air from the upper interior of said housing.

23. A directed flow bubble trap and arterial blood filter comprising:
a housing;
inlet means for permitting and controlling the upward inlet flow of arterial blood into said housing to substantially fill said housing, said inlet means including an upwardly divergent flow control member for causing a reduction in flow velocity as the arterial blood flows upward in said upwardly divergent flow control member and for causing flow with a radially outward component at the top of said upwardly divergent flow control member, said upwardly divergent flow control member being open to permit generally unobstructed radial outward flow of arterial blood at its larger end for reducing the blood velocity so that blood velocity at the top of said upwardly divergent flow control member in said housing is lower in said inlet to permit air bubbles to buoyantly rise in the top of said housing, the top of said housing having an outlet therein for the release of air collected within the top of said housing said air outlet being a self-sealing bleed port;
a blood filter member in said housing, said blood filter member having first and second sides and positioned around said upwardly divergent flow control member so that arterial blood leaving said upwardly divergent flow control member flows down around said blood filter member and reaches said first side of said filter member; and
an arterial blood outlet on said housing, said arterial blood outlet being connected to said housing so that it is positioned on the second side of said filter member so that air separated and filtered arterial blood is discharged from said arterial blood outlet.

24. A directed flow bubble trap and arterial blood filter comprising:
a housing;
inlet means for permitting and controlling the upward inlet flow of arterial blood into said housing to substantially fill said housing, said inlet means including an upwardly directed divergent flow control member for causing a reduction in flow velocity as the arterial blood flows upward in said upwardly divergent flow control member and for causing flow with a radially outward component at the top of said upwardly divergent flow control member, said upwardly divergent flow control member being open to permit generally unobstructed radial outward flow at its larger end for reducing blood velocity so that blood velocity at the top of said upwardly divergent flow control member in said housing is lower than in said inlet to permit air bubbles to rise into the top of said housing;
a blood filter member in said housing, said blood filter member having first and second sides and positioned around said upwardly divergent flow control member a blood flow control shield positioned around and extending partway down the filter member on the inlet side thereof to lengthen the arterial blood flow path to the filter member; and
an arterial blood outlet on said housing, said arterial blood outlet being connected to said housing so that it is positioned on the second side of said filter member.

* * * * *